United States Patent [19]

Cook

[11] 4,054,342
[45] Oct. 18, 1977

[54] HOSPITAL CABINET

[76] Inventor: Amy Cook, 22 Squire Lane, Bellingham, Mass. 02019

[21] Appl. No.: 684,278

[22] Filed: May 7, 1976

[51] Int. Cl.² .................. A47B 81/00; A47B 67/02
[52] U.S. Cl. ................................................ 312/209
[58] Field of Search ............... 312/203, 304, 306, 313, 312/209, 315, 310, 328, 329, 333; 5/92

[56] References Cited

U.S. PATENT DOCUMENTS

| | | | |
|---|---|---|---|
| 561,690 | 6/1896 | Pfender | 312/319 |
| 964,844 | 7/1910 | Boughton | 312/319 |
| 3,343,182 | 9/1967 | Waters | 5/92 |
| 3,446,546 | 5/1969 | D'Adamo | 312/304 |
| 3,697,363 | 10/1972 | Martinez | 312/204 |
| 3,936,107 | 2/1976 | Gourdeau | 312/204 |

*Primary Examiner*—Paul R. Gilliam
*Assistant Examiner*—Victor N. Sakran
*Attorney, Agent, or Firm*—Allen D. Brufsky

[57] ABSTRACT

A hospital cabinet including a pivotal panel which is channel-shaped to cross-section and slidably receives a planar board for use in cardio-pulmonary resuscitation.

1 Claim, 4 Drawing Figures

U.S. Patent     Oct. 18, 1977     4,054,342
FIG.1
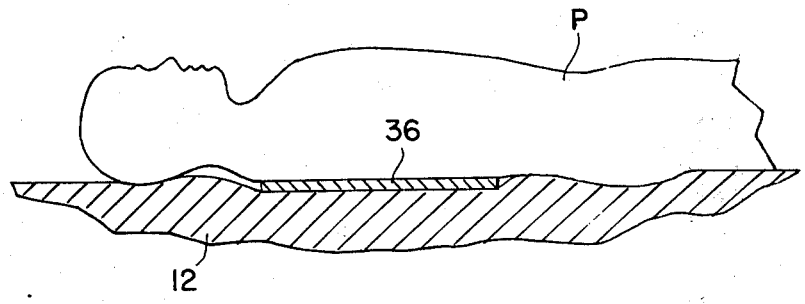
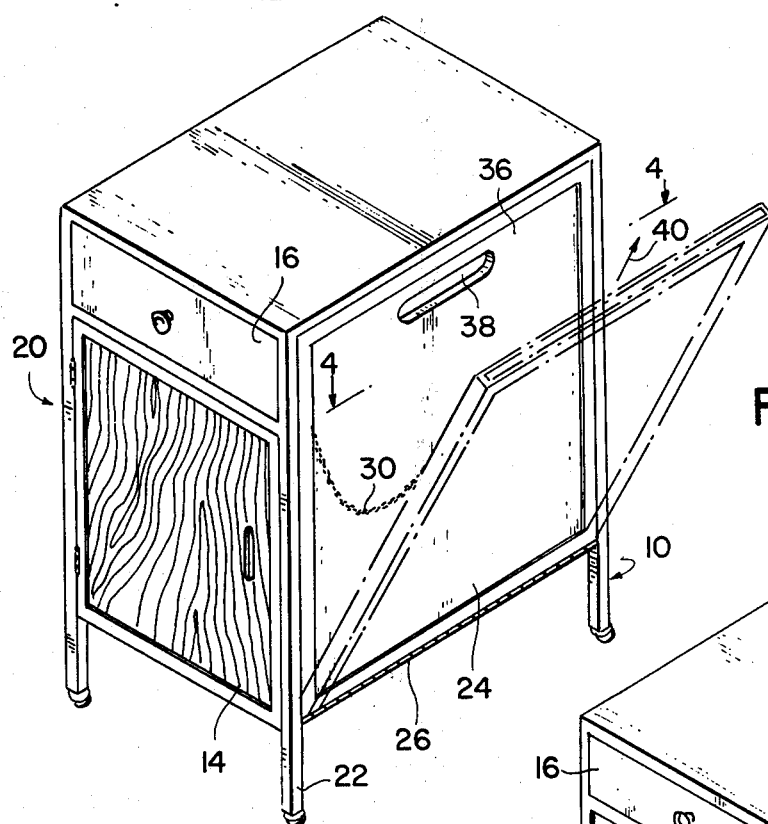
FIG.2
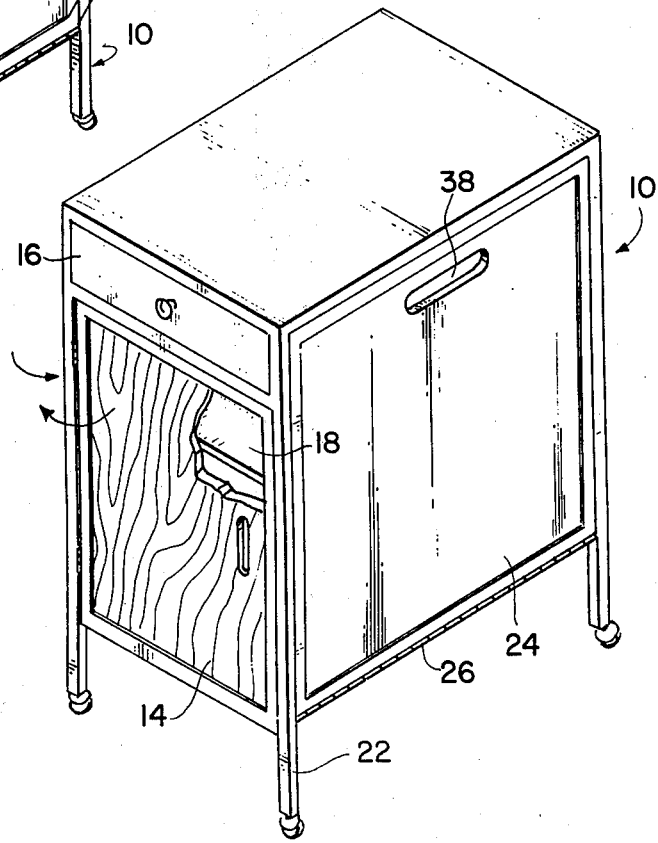
FIG.3
FIG.4
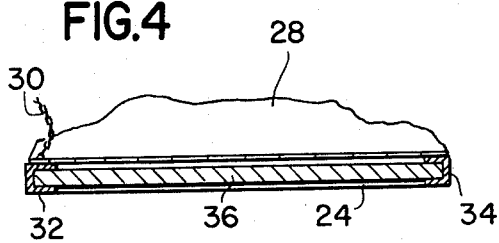

HOSPITAL CABINET

BACKGROUND OF THE INVENTION

This invention relates to a hospital cabinet, and more particularly, a hospital cabinet including equipment for use in cardio-pulmonary resuscitation.

Persons suffering a cardiac arrest are frequently in bed and the time available for revival is so critically short that it is impractical to move the patient off the bed mattress. This is true despite the fact that the presence of a soft mattress greatly impairs efforts to apply revival techniques. Likewise, persons suffering from suffocation and shock have similar needs.

Heretofore, one would have to wait for a board to arrive to be placed under the patient on the bed to provide a hard surface before attempting cardiac massage or other revival techniques. Precious seconds are lost and the chances of reviving the patient are diminished.

SUMMARY OF THE INVENTION

Accordingly, this invention provides a cabinet normally positioned beside a hospital bed which contains a hinged panel. The panel slidably receives a cardiac board. If needed, the panel is pivoted to an open position, and the board slid out of the panel. Self-closing hinges mounted the panel on the cabinet enable it to swing closed so as to be out of the way while the patient is being treated. By providing a readily accessible cardiac board near the hospital bed, precious time is saved in applying revival techniques.

BRIEF DESCRIPTION OF THE DRAWING

Further objects and advantages of the invention will become more apparent from the following description and claims, and from the accompanying drawing, wherein:

FIG. 1 is a cross-sectional view illustrating the use of a cardiac board on a hospital bed;

FIG. 2 is a perspective view of the cabinet of the present invention containing a cardiac board whose use is illustrated in FIG. 1;

FIG. 3 is a perspective view of the cabinet of FIG. 2, but illustrating the manner of withdrawing the cardiac board from its housed position in the cabinet; and FIG. 4 is a cross-sectional view taken substantially along the plane indicated by line 4—4 of FIG. 2.

DETAILED DESCRIPTION OF THE PREFERRED EMBODIMENT

Referring now to the drawing in detail, wherein like numerals indicate like elements throughout the several views, the hospital cabinet 10 of the present invention is adapted to be positioned adjacent a hospital bed containing a mattress 12.

Cabinet 10 is conventional in design in containing a front door 14, an auxiliary drawer 16, shelves 18, etc., all mounted on a housing 20 supported on four legs 22. The right side panel 24, however, is hingedly connected by a self-closing hinge 26 to the bottom 28 of housing 20. A chain 30 connected to panel 24 and the rear panel of housing 20 limits the extent of pivotal movement of panel 24 relative to the bottom 28 of housing 20.

Panel 24 is channel-shaped in cross-section, as shown in FIG. 4, and slidably receives between its opposed sides 32, 34 a wooden, planar cardiac board 36. Board 36 has a pull or indented handle 38 formed on its upper end. Board 36 is of a greater length than panel 24 so that pull 38 is exposed at all times.

If a patient P lying on mattress 12 has need of cardiac massage or pulmonary resuscitation, pull 38 on the board 36 is grasped and panel 24 pivoted about hinge 26 to an open position as shown in FIG. 2. Board 36 is then slid upwardly in the direction of arrow 40 to remove it from the channel-shaped panel 24. It is placed on mattress 12 beneath patient P and revival techniques are initiated. Chain 30 limits the pivotal movement of panel 24 and once board 36 is removed, self-closing hinge 26 causes panel 24 to close so as to be out of the way. In this manner, board 36 is readily and quickly available for use in emergencies.

To replace board 36, panel 24 is once again pivoted to an open position and board 36 slid back into the channel in panel 24 until it abuts bottom 28 of housing 20. Because panel 24 is smaller than the opening in the side of housing 20, the top of panel 24 can be grasped to pivot it about hinge 26 in the absence of board 36.

I claim:

1. A hospital cabinet comprising:
   a housing supported on a surface by a plurality of legs,
   means on said housing for mounting a planar board for use in cardio-pulmonary resuscitation, said mounting means including:
   a channel-shaped panel pivotally mounted in an opening in the side of said housing by a self-closing hinge receiving said planar board, said channel-shaped panel being smaller than said opening in the side of said housing and said planar board being substantially the same size as said housing whereby said board made be received within said panel and have an exposed portion accessible from the exterior of said housing,
   a pull on said exposed portion of said board, and
   a chain connected between said panel and housing for limiting the extent of pivotal movement of said panel relative to said housing.

* * * * *